United States Patent [19]

Ohuchi et al.

[11] Patent Number: 5,571,820

[45] Date of Patent: Nov. 5, 1996

[54] HETEROCYCLIC COMPOUND

[75] Inventors: Yutaka Ohuchi; Masaji Suzuki; Hajime Asanuma; Sadakazu Yokomori; Katsuo Hatayama; Yoshihiko Isobe; Chika Ito; Makoto Muramatsu, all of Tokyo, Japan

[73] Assignee: Taisho Pharmaceutical Co., Ltd., Japan

[21] Appl. No.: 428,119

[22] PCT Filed: Oct. 15, 1993

[86] PCT No.: PCT/JP93/01484

§ 371 Date: Apr. 28, 1995

§ 102(e) Date: Apr. 28, 1995

[87] PCT Pub. No.: WO94/12497

PCT Pub. Date: Jun. 9, 1994

[30] Foreign Application Priority Data

Nov. 20, 1992 [JP] Japan ................... 4-311653

[51] Int. Cl.⁶ .................. C07D 451/04; A61K 31/46
[52] U.S. Cl. ................... 514/304; 546/126
[58] Field of Search ................ 546/126; 514/304

[56] References Cited

U.S. PATENT DOCUMENTS 5,106,851  4/1992  Turconi et al. .................. 514/259

5,248,684  9/1993  Suzuki et al. .................. 514/299

FOREIGN PATENT DOCUMENTS 3197462  8/1991  Japan .
4226980  8/1992  Japan .

*Primary Examiner*—David B. Springer
*Attorney, Agent, or Firm*—Lorusso & Loud

[57]  ABSTRACT

Endo-N-(8-methyl-8-azabicyclo[3.2.1]oct-3-yl)-1-isopropyl-2(1H)-quinolone-3-carboxamide shown by formula (I):

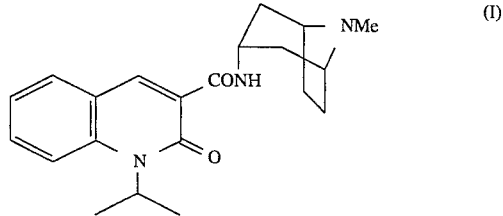

or an acid addition salt thereof exhibits a potent action for stimulating a serotonin 4 receptor and is effective for the treatment of diseases and for the improvement of conditions, caused by a reduced motility in the gastrointestinal tract.

13 Claims, No Drawings

HETEROCYCLIC COMPOUND

This application is a 371 of PCT/JP 93/01484 filed Oct. 15, 1993.

TECHNICAL FIELD

The present invention relates to a heterocyclic compound. More particularly, the present invention relates to a novel quinolone compound, which has an action for stimulating a serotonin 4 receptor and is therefore useful for the treatment of chronic gastritis or for improving digestive tract conditions accompanied by postoperative gastroparesis. The present invention also relates to a pharmaceutical use of such a quinolone compound.

BACKGROUND ART

Serotonin is a nurotransmitter which is widely distributed in human and has a remarkable variety of physiological effects. It is hitherto known that a serotonin receptor includes three subtypes of serotonin 1 receptor, serotonin 2 receptor and serotonin 3 receptor. In addition to these receptors, it is reported by Dumuis, A., et al., Molecular Pharmacology, 34, 880, 1988 that serotonin 4 receptor is existent.

Serotonin 4 receptor is considered to take a part in contraction of the ileum or ascending colon of guinea pig or relaxation of rat esophagus. Cisapride and renzapride, which are stimulants of serotonin 4 receptor, accelerate gastrointestinal motor functions and improve gastrointestinal conditions such as chronic gastritis, heartburn accompanied by postoperative gastroparesis, anorexia, bowel pain, abdominal distension, etc., and are thus considered to be effective for the treatment of gastro-esophagal reflux, intestinal pseudo-obstruction and constipation [Alimentary Pharmacology and Therapeutics, 6, 273, 1992].

As heterocyclic compounds having an activity of antagonizing or stimulating serotonin receptors, European Patent No. 0458636A1 discloses quinolone derivatives which exert on a serotonin 3 receptor antagonizing activity.

On the other hand, U.S. Pat. No. 5,106,851 discloses quinazoline-carboxylic acid derivatives as heterocyclic compounds effective for the treatment of gastrointestinal disorders. However, the compounds are merely known to show an affinity to muscarinic receptors but remain unknown about any action of serotonin receptors.

As stated above, no research has been reported on any heterocyclic compound having an excellent antagonizing or stimulating activity particularly on serotonin 4 receptor.

Accordingly, the .object of the present invention is to provide a novel heterocyclic compound having a potent stimulating activity especially on serotonin 4 receptor and a pharmaceutical use thereof.

DISCLOSURE OF INVENTION

An object of the present invention is to provide endo-N-(8-methyl-8-azabicyclo[3.2.1]oct-3-yl)-1-isopropyl-2(1H)-quinolone-3-carboxamide represented by formula (I):

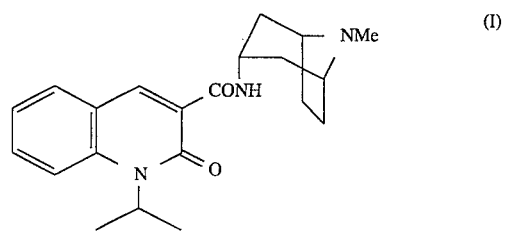

as well as a pharmaceutically acceptable salt thereof.

Another object of the present invention is to provide a pharmaceutical composition comprising as an effective ingredient the compound of formula (I) or its pharmaceutically acceptable salt and a pharmaceutically acceptable carrier, particularly for stimulating serotonin 4 receptor.

A further object of the present invention is to provide a method for stimulating serotonin 4 receptor which comprises administering to human an effective dose of the compound of formula (I) or a pharmaceutically acceptable salt thereof.

A still further object of the present invention is to provide the compound of formula (I) or a pharmaceutically acceptable salt thereof, for use as an active ingredient of the pharmaceutical composition particularly for stimulating serotonin 4 receptor.

A still further object of the present invention is to provide use of said compound or a salt thereof for the preparation of a pharmaceutical composition comprising as an effective ingredient the compound of formula (I) or a pharmaceutically acceptable salt thereof and for stimulating serotonin 4 receptor.

BEST MODE FOR CARRYING OUT THE INVENTION

As the pharmaceutically acceptable salts of the compound of formula (I) in accordance with the present invention, there are acid addition salts. These acid addition salts are those obtained by adding pharmacologically acceptable acids to the nitrogen atom in the molecule of the compound of formula (I) and include salts of mineral acids such as hydrochloric acid, hydrobromic acid, hydroiodic acid, sulfuric acid, nitric acid or phosphoric acid; salts of organic acids such as acetic acid, oxalic acid, citric acid, tartaric acid, maleic acid, succinic acid, fumaric acid, p-toluenesulfonic acid, benzenesulfonic acid or methanesulfonic acid.

The compound of the present invention represented by formula (I) (hereinafter Compound (I)) can be produced, for example, by a process shown in the following production scheme.

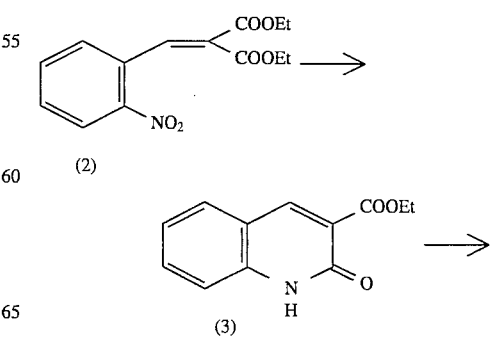

-continued
Production scheme

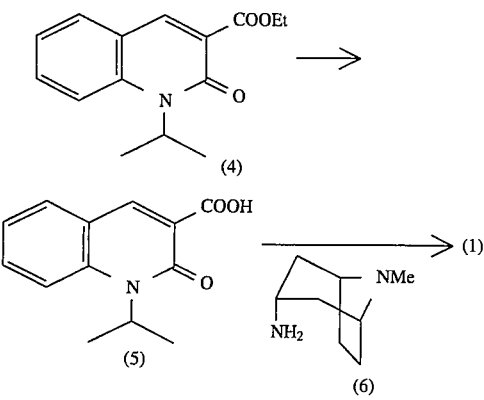

Compound (2) used as the starting compound can be prepared by the method disclosed in J. Chem. Soc., 346, 1960.

For reductive ring closure from Compound (2) to Compound (3), reaction conditions for conventional reduction of a nitro group may be employed. The reduction and ring closure take place simultaneously to obtain Compound (3). Examples of reaction conditions for the reduction include:

(1) catalytic reduction in an appropriate solvent using palladium-carbon or platinum; and (2) reduction in an appropriate inert solvent using iron or tin, or using sodium sulfide-ammonium chloride.

The reduction in (1) above proceeds in a solvent and examples of the solvent are water; acetic acid; an alcohol; a hydrocarbon such as hexane; an ether such as diethyl ether and tetrahydrofuran; a non-protic polar solvent such as N,N-dimethylformamide; and a solvent mixture thereof. As a solvent employed in the reduction in (2) above, there are mentioned, for example, water, acetic acid, methanol, ethanol and dioxane, and a solvent mixture thereof.

The reaction temperature for the reduction in the reactions (1) and (2) ranges generally from 0° C. to the boiling point of a solvent used; the reaction time is appropriately between 30 minutes and 12 hours.

Compound (3) is converted by N-isopropylation into Compound (4) under conventional conditions for N-alkylation of an acid amide. More specifically, N-isopropylation is carried out in an appropriate solvent in the presence of a base, for example, a metal alkali such as sodium and potassium; alkali hydride such as sodium hydride; an alkali alkoxide such as sodium ethoxide and potassium tertiary butoxide; an alkali hydroxide such as sodium hydroxide and potassium hydroxide; a carbonate such as sodium carbonate and potassium carbonate; an amine such as triethylamine and pyridine.

Examples of the solvent used for the N-isopropylation are an alcohol such as methanol and ethanol; an ether such as diethyl ether, dioxane and tetrahydrofuran; a hydrocarbon such as hexane and benzene; a non-protic polar solvent such as N,N-dimethylformamide; or a solvent mixture thereof. The reaction is performed generally at 0° C. up to the boiling point of a solvent used.

In general, the reaction time is appropriately set for 30 minutes to 12 hours.

For introducing the isopropyl group into Compound (3), there is employed a reactive derivative such as an isopropyl halide, e.g., isopropyl iodide.

Hydrolysis from Compound (4) to Compound (5) is performed under conventional conditions for hydrolysis, for example, acidic hydrolysis using hydrochloric acid or acetic acid, alkaline hydrolysis using sodium hydroxide. The reaction temperature is generally between 0° C. and the boiling point of a solvent used. In general, the reaction time is appropriately set in the range of 30 minutes to 12 hours.

Compound (5) is converted into Compound (1) by amidation of Compound (5) or its reactive derivative with endo-3-amino-8-methyl-8-azabicyclo[3.2.1]octane (Compound (6)). Thus Compound (1) can be prepared.

The amidation may be carried out in a conventional manner.

For the amidation, there may be employed a method which comprises suitably reacting a reactive derivative of Compound (5), e.g., its acid halide, lower alkyl ester or activated ester, or its imidazolide or mixed anhydride with the aforesaid octane compound; or a method which comprises directly binding Compound (5) to Compound (6) using a condensing agent.

Where the acid halide is employed, the halide of Compound (5) is reacted with Compound (6) generally in a solvent inert to the reaction at a temperature of from 0° C. to the boiling point of the solvent in the presence of or absence of a base.

Examples of the solvent include ether, tetrahydrofuran, dioxane, methylene chloride, chloroform, dichloroethane, benzene, toluene, xylene, water or a mixture thereof.

Examples of the base which can be employed are potassium carbonate, sodium hydroxide, potassium hydroxide, pyridine, triethylamine and N,N-dimethylaniline.

In general, the reaction time is appropriately in the range of 30 minutes to 12 hours.

Where the compounds are directly bound to each other using a condensing agent, Compound (5) is reacted with Compound (6) generally in a solvent inert to the reaction at a temperature of from 0° C. to the boiling point of the solvent used in the presence of a condensing agent.

As the solvent, those mentioned above may be used in a similar manner.

Examples of the condensing agent which can be employed are dicyclohexylcarbodiimide, 2-chloro-N-methylpyridinum iodide and diphenylphosphorylazide.

Compound (6) can be prepared by the method described in J. Am. Chem. Soc., 79, 4194, 1957.

Compound (4) or (5) in the reaction scheme described hereinabove may also be prepared by the process shown below:

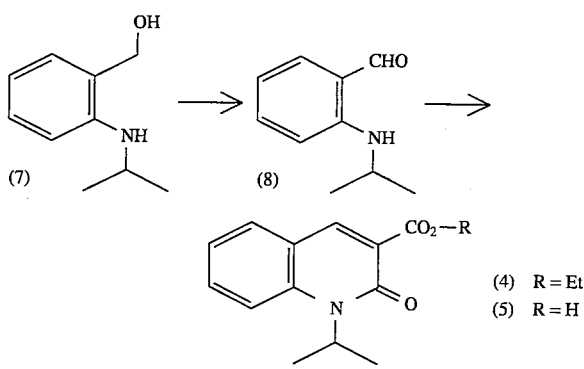

Compound (8) can be prepared by oxidizing Compound (7) with an oxidizing agent such as 2,3-dichloro-5,6-dicyano-1,4-benzoquinone (DDQ) in a solvent such as dioxane.

Compound (8) may be converted into Compound (4) or (5) by condensing Compound (8) with malonic acid or a malonic acid ester in the presence of or absence of a condensing agent.

Examples of the condensing agent which can be used include a hydroxide, carbonate, hydrogen carbonate, alcoholate and amide of an alkali metal; an amine such as ammonia and piperidine, acetic acid, acetic anhydride and zinc chloride. The condensing agents may be used alone or in admixture. Using Compound (4) or (5), the compound of the present invention can be prepared by the process as described above.

Toxicity of the compound represented by formula (1) which is the effective ingredient of the pharmaceutical composition of the present invention was examined in terms of toxicity by mouse single administration (acute toxicity). The results indicate that the minimum lethal dose is more than 125 mg/kg by oral administration.

A dose of the compound represented by formula (1) which is the effective ingredient of the pharmaceutical composition of the present invention varies depending upon condition. In general, a daily dose for adult is in the range of 0.1 to 100 mg/human for oral administration and 0.01 to 20 mg/human for intravenous administration. The dose may be given at once or by dividing the daily dose into 2 to 4 times.

The pharmaceutical composition of the present invention is prepared for use into a solid preparation such as a tablet, a pill, a capsule or granules, or into an injection, liquid, an emulsion or a suppository.

These pharmaceutical preparations may be made in a conventional manner for preparing medical compositions. If necessary and desired, an additive which is conventionally used may be added to the preparations; examples of such an additive are an aid, a stabilizer, an emulsifier and a diluent.

Hereinafter the compound of formula (1) which is the effective ingredient of the pharmaceutical composition of the present invention is specifically described with respect to its serotonin 4 receptor stimulating activity, activity of stimulating various gastrointestinal motor functions, and its toxicity.

Experiment 1. Serotonin 4 Receptor Stimulating Activity
Compounds Tested

The compounds shown in the following Table 1 were examined.

TABLE 1

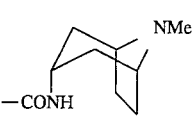

| Cpd. No. | R₁ | R₂ | R₃ |
|---|---|---|---|
| Cpd. of the invention |   |   |   |
| 1 | isopropyl | H | 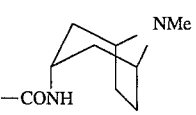 |
| Cpds. for comparison |   |   |   |
| 2 | ethyl | H | 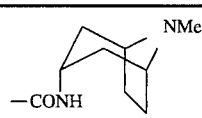 |

TABLE 1-continued

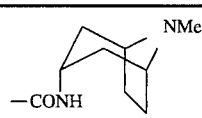

| Cpd. No. | R₁ | R₂ | R₃ |
|---|---|---|---|
| 3 | n-propyl | H | 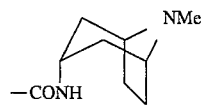 |
| 4 | n-butyl | H | 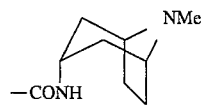 |
| 5 | isobutyl | H | 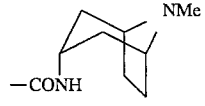 |
| 6 Cpd. of USP 5,106,851 | H | H | 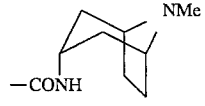 |
| 7 Cpd. of EP 0458636A1 | n-butyl | OH | 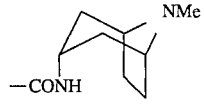 |

Method

Twitch responses were examined in longitudinal muscle strips of guinea pig by a modification of the method described in The Journal of Pharmacology and Experimental Therapeutics, 252, 1378, 1990.

From Hartley guinea pigs, a section of ileum 25 cm in length and proximal to the ileocecal junction was removed. The longitudinal muscle strips obtained from two segments of ileum about 4 cm each in length were used for this experiment. The longitudinal muscle strips were suspended in Krebs' solution at 32° to 34° C. and bubbled with 95% $O_2$ and 5% $CO_2$ under a load of about 0.8 g. Twitch responses were recorded under electrical stimulation of 0.2 Hz, 1 msec pulse duration, using force displacement transducers. The longitudinal muscle strips, stimulated at supramaximal voltage, were allowed to equilibrate for about an hour. After it was confirmed that the twitch responses were enhanced by $10^{-8}$ M 5-hydroxytryptamine (5-HT), each agonist was examined on its activity for twitch responses. The test was carried out by exposing the strips to cumulative additions of agonist at least at 45-minute intervals.

Results $ED_{50}$ of the serotonin 4 receptor stimulating activity is shown in Table 2 below.

TABLE 2

| Compound Tested | $ED_{50}$ (nM) |
|---|---|
| Compound of this invention |   |
| 1 | 21.4 |

TABLE 2-continued

| Compound Tested | ED$_{50}$ (nM) |
|---|---|
| Compound for Comparison | |
| 2 | 138 |
| 3 | 413 |
| 4 | >3000 |
| 5 | 974 |
| 6 | >3000 |
| 7 | >3000 |

As is appreciated from the results shown in Table 2, the compound of the present invention exhibited a much more potent serotonin 4 receptor stimulating activity than any of the other compounds having an alkyl group other than isopropyl, i.e., Compounds 2 to 5 for comparison, Comparative Compound 6 recited in U.S. Pat. No. 5,106,851 and Comparative Compound 7 recited in EP 0458636A1.

Experiment 2. Activity on Gastric Motility in Rat

Method:

Male Wistar rats weighing 250 to 350 g were fasted for 18 hours and then provided for experiment. The abdominal cavity was opened under ether anesthesia and a rubber balloon was inserted into the stomach via the forestomach. A cannula for administering a drug was put in the peritoneal cavity. After recovery from the anesthesia, the balloon was connected to low pressure transducers to record gastric motility in the conscious state.

The compound of the present invention was suspended in physiological saline and the suspension was intraperitoneally administered.

Contraction frequency and motility index are shown in terms of a proportion (%) of a mean value calculated for 15 minutes to a value prior to administration (0 minute). The value for 0 minute was made a mean value for 30 minutes prior to the administration.

Results

The compound of the present invention accelerated the gastric motility in a dose of 1 mg/kg, i.p. On the other hand, no affect was noted with the vehicle alone.

Changes in contraction frequency and motility index caused by administration of the compound of the present invention are shown in Table 3 below.

TABLE 3

| | Time after administration (minute) | | | | | | |
|---|---|---|---|---|---|---|---|
| | 0 | 10 | 20 | 30 | 40 | 50 | 60 |
| Contraction frequency (%) | 100 | 182.3 | 243.5* | 187.0 | 134.7 | 134.9 | 141.6 |
| Motility index (%) | 100 | 169.3 | 188.1 | 144.2 | 83.3 | 88.8 | 108.8 |

*: $P < 0.05$, $N = 4$

Experiment 3. Activity on Gastrointestinal Motor in Dogs

The activity was determined by a modification of the method described in Gastroenterologia Japonica, 12, 275, 1977.

Method

Beagle dogs of both sexes weighing 9 to 15 kg were anesthetized with sodium pentobarbital and strain gauge force transducers were sutured on five (5) portions, i.e., for determining antral, duodenum, jejunal, ileal and colonal motor responses. A cannula for administering a drug was mounted persistently into the jugular vein. After recovery of the surgery, motor responses at those portions on the gastrointestinal tract in both during a fasting period and after feeding were determined in the conscious dogs.

The compound of the present invention was administered by dissolving the compound in 5% lactate saline aqueous solution for intravenous injection and for oral administration by suspending the compound in 5% gum arabic aqueous solution.

The motor index is shown in terms of a proportion (%) of a mean value calculated for 15 minutes to a value prior to administration (0 minute). The value for 0 minute was made a mean value for 30 minutes prior to the administration.

Results

The compound of the present invention showed acceleration on the motor action of the gastrointestinal tract by intravenous and oral administration, both during the fasting period and after feeding. On the other hand, no influence was noted when the vehicle alone was given.

Tables 4 and 5 below indicate the activity of the compound of the present invention in doses of 0.3 mg/kg intravenously and 1 mg/kg orally, respectively, on the gastric motor action after feeding.

TABLE 4

| | Intravenous Administration | | | | | | | | |
|---|---|---|---|---|---|---|---|---|---|
| | Time after administration (min) | | | | | | | | |
| | 0 | 15 | 30 | 45 | 60 | 75 | 90 | 105 | 120 |
| Motility index (%) | 100 | 371.4 | 322.6 | 282.3* | 261.1* | 281.9** | 262.1* | 242.9* | 195.2 |

*: $P < 0.05$, **: $P < 0.01$, $N = 3$

TABLE 5

| | Oral Administration | | | | | | | | | | |
|---|---|---|---|---|---|---|---|---|---|---|---|
| | Time after administration (min) | | | | | | | | | | |
| | 0 | 15 | 30 | 45 | 60 | 75 | 90 | 105 | 120 | 180 | 210 | 240 |
| Motility index (%) | 100 | 116.4 | 193.5 | 191.4* | 206.9** | 202.2* | 192.5* | 207.3* | 194.9 | 195.8 | 176.2 | 182.8 |

*: $P < 0.05$, **: $P < 0.01$, $N = 3$

Experiment 4. Activity on Gastric Emptying in Rat

The activity was investigated by a modification of the method described in British Journal of Pharmacology, 91, 263, 1987.

Method

Male Wistar rats weighing 170 to 220 g were used which were deprived of food for 24 hours. Glass spheroids of 500 mg/ml were orally administered to the animal in a dose of 1 ml 30 minutes after subcutaneous administration or 60 minutes after oral administration, of drugs. The glass spheroids remained in the stomach were recovered and their weight was measured to determine gastric emptying to control motility.

The compound of the present invention was suspended in physiological saline and the resulting suspension was administered.

Results

The compound of the present invention dose-dependently accelerated gastric emptying in both oral and subcutaneous administration, as shown in Table 6 below.

TABLE 6

| Route for administration | Dose (mg/kg) | No. of Case | Residual rate in stomach (%) |
|---|---|---|---|
| p.o. | 0.03 | 5 | 67.3 |
|  | 0.3 | 5 | 64.5 |
|  | 3.0 | 6 | 42.0 |
| s.c. | 0.1 | 5 | 51.8 |
|  | 1.0 | 5 | 50.3 |
|  | 10.0 | 4 | 36.8 |

Experiment 5. Activity on Intestinal Transit in Mice

The activity was determined by a modification of the method described in YAKURI-TO-CHIRYO, 10, 195, 1982.

Method

Male ICR mice weighing 20 to 30 g were used which were deprived of food for 24 hours. A suspension containing 5% carbon powder gum arabic was orally administered to the animal in a dose of 1 ml 15 minutes after subcutaneous administration or 30 minutes after oral administration, of drugs. The intestinal tract was removed 20 minutes after. The entire length of the intestinal tract and the distance of the carbon powders moved were measured, and a moving rate was calculated for control animal.

Results

The compound of the present invention accelerated the intestinal transit in both oral and subcutaneous administration, as shown in Table 7 below.

TABLE 7

| Route for administration | Dose (mg/kg) | No. of Case | Intestinal transit (%) |
|---|---|---|---|
| p.o. | 1 | 5 | 100.6 |
|  | 3 | 5 | 121.4 |
|  | 10 | 6 | 120.4 |
| s.c. | 1 | 5 | 116.6 |
|  | 3 | 4 | 117.8 |
|  | 10 | 6 | 138.3** |

**: $P < 0.01$

Experiment 6. Toxicity on Consecutive 14-day Oral Administration in Rat

Toxicity of consecutive oral administration was investigated by oral administration of male Wistar rats of 5 weeks age, weighing 124 to 140 g and seven rats forming one group, orally received the compound of the present invention for 14 consecutive days in a daily dose of 100 mg/kg or 250 mg/kg once a day. During the course of administration, general conditions were observed and the body weight was measured. At the time when the administration was completed, hematological inspection, hematochemical inspection, urinalysis, anatomical finding, organ weight measurement and pathohistological inspection were performed. In the 250 mg/kg group, prevention of body weight increase was noted and secondary changes accompanied by aggravation of general conditions were observed in the liver, thymus, adrenogenital organ, adrenal, etc. However, no toxic change was noted in the 100 mg/kg group. Taking into account the pharmacological activities of the compound of the present invention, the toxicity is reasonably assumed to be weak.

Hereinafter the present invention will be described below more specifically, with reference to Preparation Examples and Examples.

PREPARATION EXAMPLE 1

Preparation of endo-N-(8-methyl-8-azabicyclo[3.2.1]oct-3-yl)-1-isopropyl-2(1H)-quinolone-3-carboxamide 1) Ethyl 2(1H)-quinolone-3-carboxylate In 700 ml of acetic acid was dissolved 45 g of diethyl 2-nitrobenzylidenemalonate (J. Org. chem., 3462, 1960). While maintaining at 80° C., 53 g of iron powders were added by several portions to the solution. The mixture was stirred for further 2 hours.

After the system was reverted to room temperature, the reaction mixture was filtered through celite and the filtrate was concentrated in vacuo. The thus obtained oily substance was purified by silica gel column chromatography (chloroform:methanol=10:1) to give 21.3 g of ethyl 2(1H)-quinolone-3-carboxylate.

mp: 160°–163.2° C. (ethyl acetate)

2) Ethyl 1-isopropyl-2(1H)-quinolone-3-carboxylate

After 20 g of ethyl 2(1H)-quinolone-3-carboxylate was added to a solution of 4.45 g of sodium hydride in 100 ml of DMF, 31.5 g of isopropyl iodide was added to the mixture followed by stirring at 70° C. for 8 hours. After DMF was removed by distillation in vacuo, the residue was poured into water. The mixture was then extracted with ethyl acetate. After the organic layer was washed with water and then with saturated sodium chloride aqueous solution, the organic layer was dried over anhydrous sodium sulfate.

The solvent was distilled off in vacuum. The resulting oily substance was purified by silica gel column chromatography (ethyl acetate:n-hexane=4:1) to obtain 1.55 g of ethyl 1-isopropyl-2(1H)-quinolone-3-carboxylate.

mp: 54°–57° C. (ethyl acetate)

3) 1-Isopropyl-2(1H)-quinolone-3-carboxylic acid

A solution of 1.55 g of ethyl 1-isopropyl- 2(1H)-quinolone-3-carboxylate and 0.28 g of sodium hydroxide in a mixture of 10 ml of ethanol and 2 ml of water was stirred overnight at room temperature. After the solvent was distilled off, dil. hydrochloric acid was added to the residue. The precipitated solid was taken by filtration, washed with water and dried to give 1.22 g of 1-isopropyl-2(1H)-quinolone-3-carboxylic acid.

mp: 168°–169° C. (ethyl acetate)

4) Endo-N-(8-methyl-8-azabicyclo[3.2.1]oct-3-yl)-1 -isopropyl-2(1H)-quinolone-3-carboxamide A solution of 0.5 g of 1-isopropyl-2(1H)-quinolone-3-carboxylic acid in 5 ml of thionyl chloride was stirred for 2 hours at reflux. After thionyl chloride was completely distilled off in vacuo, 3 ml of benzene was added to the residue. Under ice cooling, 3 ml of benzene containing 0.36 g of endo-3-amino-8-methyl-8-azabicyclo[3.2.1]octane was dropwise added to the benzene solution of the acid chloride described above. The mixture was stirred for 2 hours at room temperature. After ethyl acetate was added to the reaction mixture, the organic layer was washed with water and then with saturated sodium bicarbonate aqueous solution followed by drying over anhydrous magnesium sulfate. After the solvent was distilled off in vacuo, the residue was purified by alumina column chromatography (chloroform) and recrystallized from ethyl acetate to give 0.39 g of endo-N-(8-methyl-8-azabicyclo[3.2.1]oct-3-yl)-1-isopropyl-2(1H)-quinolone-3-carboxamide.

mp: 175.8°–177.8° C. (ethyl acetate)

MS (m/z): 353($M^+$), 214, 172, 84

IR ν ($cm^{-1}$, KBr): 3263, 1673, 1528, 1206

NMR (ppm, $CDCl_3$): 1.68 (6H, d, J=7.2 Hz), 1.76 (1H, s), 1.83 (1H, s), 2.00–2.40 (6H, m), 2.34 (3H, s), 3.10–3.28 (2H, m), 4.30 (1H, q, J=7.2 Hz), 5.40–5.90 (1H, m), 7.22–7.33 (1H, m), 7.55–7.70 (2H, m), 7.75 (1H, d, J=7.8 Hz), 8.83 (1H, s), 10.48 (1H, d, J=7.2 Hz)

Elemental analysis for $C_{21}H_{27}N_3O_2$: Calcd. (%) C, 71.36; H, 7.70; N, 11.88. Found (%) C, 71.21; H, 7.67; N, 11.84.

PREPARATION EXAMPLE 2

Preparation of endo-N-(8-methyl-8-azabicyclo[3.2.1]oct-3-yl)-1-isopropyl-2(1H)-quinolone-3-carboxamide 1) 2-Isopropylaminobenzyl alcohol While maintaining at 0° to 5° C., 10 g of sodium borohydride was added by several portions to a mixture of 10 g of 2-aminobenzyl alcohol, 13.3 g of sodium acetate trihydrate, 40 ml of acetic acid, 80 ml of water, 30 ml of ethanol and 30 ml of acetone. After stirring for an hour at the same temperature, the reaction mixture was neutralized with sodium hydrogen carbonate followed by extraction with ethyl acetate. The organic layer was washed with water and then with saturated sodium chloride aqueous solution followed by drying over anhydrous magnesium sulfate. After the solvent was distilled off in vacuo, the resulting oily substance was purified by silica gel column chromatography (hexane:ethyl acetate=2:1) and then distilled in vacuo to give 9.6 g of 2-isopropylaminobenzyl alcohol.

bp: 110°–114° C. (4 m Hg)

2) 2-Isopropylaminobenzaldehyde

After 13.2 g of 2,3-dichloro-5,6-dicyano-1,4-benzoquinone (DDQ) was added by several portions to a solution of 9.6 g of 2-isopropylaminobenzyl alcohol in 200 ml of dioxane, the mixture was stirred for further an hour. The solvent was removed by distillation to concentrate the reaction mixture, and methylene chloride was then added thereto followed by filtration. The filtrate was concentrated and the resulting oily substance was purified by silica gel column chromatography (n-hexane:ethyl acetate=5:1) to obtain 7.6 g of 2-isopropylaminobenzaldehyde.

NMR (ppm, $CDCl_3$): 1.27 (6H, d, J=6.4 Hz), 3.67–3.83 (1H, m), 6.59–6.73 (2H, m), 7.31–7.43 (1H, m), 7.44 (1H, dd, J=7.6, 1.4 Hz), 8.26 (1H, s), 9.79 (1H, s).

3) Ethyl 1-isopropyl-2(1H)-quinolone-3-carboxylate

A solution of 7.5 g of 2-isopropylaminobenzaldehyde, 11.0 g of diethyl malonate and 11.6 g of sodium hydrogen carbonate in 80 ml of acetic anhydride was stirred at 100° C. for 15 hours. After the solvent was removed by distillation in vacuo, water was added to the residue. The mixture was then extracted with ethyl acetate. After the organic layer was washed with water and then with saturated sodium bicarbonate aqueous solution, the organic layer was dried over anhydrous sodium sulfate. The solvent was distilled off in vacuum. The resulting oily substance was purified by silica gel column chromatography (n-hexane:ethyl acetate=4:1) to obtain 7.3 g of ethyl 1-isopropyl-2(1H)-quinolone-3-carboxylate.

4) Endo-N-(8-methyl-8-azabicyclo[3.2.1]oct-3-yl)-1-isopropyl-2(1H)-quinolone-3-carboxamide The procedures were carried out in a manner similar to Preparation Examples 1–4) and 1–5) to give endo-N-(8-methyl-8-azabicyclo[3.2.1]oct-3-yl)-1-isopropyl-2(1H)-quinolone-3-carboxamide.

PREPARATION EXAMPLE 3

Preparation of endo-N-(8-methyl-8-azabicyclo[3.2.1]oct-3-yl)-1-isopropyl-2(1H)-quinolone-3-carboxamide hydrochloride In 3 ml of tetrahydrofuran was dissolved 100 mg of endo-N-(8-methyl-8-azabicyclo[3.2.1]oct-3-yl)-1-isopropyl-2(1H)-quinolone-3-carboxamide. The solution was acidified by adding an aqueous hydrochloric acid. The precipitated crystals were taken out by filtration and dried to give 107 mg of endo-N-(8-methyl-8-azabicyclo[3.2.1]oct-3-yl)-1-isopropyl-2(1H)-quinolone-3-carboxamide hydrochloride.

mp: 267°–270° C.

PREPARATION EXAMPLE 4

Preparation of endo-N-(8-methyl-8-azabicyclo[3.2.1]oct-3-yl)-1-isopropyl-2(1H)-quinolone-3-carboxamide maleate In 3 ml of ethyl acetate was dissolved 100 mg of endo-N-(8-methyl-8-azabicyclo[3.2.1]oct-3-yl)-1-isopropyl-2(1H)-quinolone-3-carboxamide. To the solution was added 3 mg of maleic acid. The precipitated crystals were taken out by filtration and dried to give 106 mg of endo-N-(8-methyl-8-azabicyclo[3.2.1]oct-3-yl)-1-isopropyl-2(1H)-quinolone-3-carboxamide maleate.

mp: 207°–210° C.

Pharmaceutical Composition

Tablet

Composition (Per Tablet)

| | |
|---|---|
| Compound of this invention | 2 mg |
| Lactose | 19 mg |
| Potato starch | 20 mg |
| Crystalline cellulose | 28 mg |
| Carboxymethyl cellulose | 20 mg |
| Hydroxymethyl cellulose | 10 mg |
| Magnesium stearate | 1 mg |

Method

After 20 g of the compound of this invention, 190 g of lactose, 20 g of potato starch, 280 g of crystalline cellulose, 200 g of carboxymethyl cellulose and 100 g of hydroxymethyl cellulose were blended with each other, the mixture was ground into powders with a crusher and then stirred. The powders were put in a granulator and a small quantity of water was added to the powders for granulation. The granules were then dried with a fluid bed drier and 10 g of magnesium stearate was added to the granules. The mixture was tableted with a tableting machine to obtain tablets each 100 mg in weight and 6 mm in diameter, containing 2 mg of the compound of the present invention.

Industrial Applicability

The compound of the present invention acts on a serotonin 4 receptor thereby to exert on a serotonin-like receptor stimulating activity. More specifically, the compound of the present invention exhibits an action of activating gastrointestinal motor functions to improve gastrointestinal conditions such as chronic gastritis, heartburn accompanied by postoperative gastroparesis, anorexia, bowel pain, abdominal distension, etc., and are thus effective for the treatment of gastro-esophagal reflux, intestinal pseudo-obstruction and constipation.

We claim:

1. Endo-N-(8-methyl-8-azabicyclo[3.2.1]oct-3-yl)- 1-isopropyl-2(1H)-quinolone-3-carboxamide or a pharmaceutically acceptable salt thereof.

2. A pharmaceutical composition comprising as an effective ingredient the compound according to claim 1 or a pharmaceutically acceptable salt thereof and a pharmaceutically acceptable carrier.

3. A pharmaceutical composition according to claim 2, which is for stimulating a serotonin 4 receptor.

4. A pharmaceutical composition according to claim 2, which is for activating a gastrointestinal motor function.

5. A method for stimulating a serotonin 4 receptor which comprises administering to human an effective dose of the compound or a pharmaceutically acceptable salt thereof according to claim 1.

6. A method according to claim 5, which is for activating a gastrointestinal motor function.

7. A compound or a pharmaceutically acceptable salt thereof according to claim 1, for use as an effective ingredient of a pharmaceutical composition.

8. A compound or a pharmaceutically acceptable salt thereof according to claim 7, wherein said pharmaceutical composition is a pharmaceutical composition for stimulating a serotonin 4 receptor.

9. A compound or a pharmaceutically acceptable salt thereof according to claim 7, wherein said pharmaceutical composition is a pharmaceutical composition for activating a gastrointestinal motor function.

10. Use of a compound or a pharmaceutically acceptable salt thereof according to claim 1, for the preparation of a pharmaceutical composition comprising as an effective ingredient said compound or a pharmaceutically acceptable salt thereof and for stimulating a serotonin 4 receptor.

11. Use according to claim 10, wherein said pharmaceutical composition is a pharmaceutical composition for activating a gastrointestinal motor function.

12. A pharmaceutical composition according to claim 3, which is for activating a gastrointestinal motor function.

13. A compound of a pharmaceutically acceptable salt thereof according to claim 8, wherein said pharmaceutical composition is a pharmaceutical composition for activating a gastrointestinal motor function.

* * * * *